United States Patent [19]

Nelan

[11] 4,226,785

[45] Oct. 7, 1980

[54] PROCESS FOR DEHYDROGENATION OF STEROLS TO PRODUCE Δ4-3-KETOSTEROIDS

[75] Inventor: Donald R. Nelan, Kingsport, Tenn.

[73] Assignee: Eastman Kodak Company, Rochester, N.Y.

[21] Appl. No.: 81,954

[22] Filed: Oct. 4, 1979

[51] Int. Cl.³ .............................................. C07J 71/00
[52] U.S. Cl. ................................................... 260/397.25
[58] Field of Search ..................................... 260/397.25

[56] References Cited

U.S. PATENT DOCUMENTS

| 3,450,541 | 6/1969 | Schwartz et al. | 260/397.25 |
| 4,057,541 | 11/1977 | Weber et al. | 260/397.25 |

*Primary Examiner*—Elbert L. Roberts
*Attorney, Agent, or Firm*—Clyde L. Tootle; Daniel B. Reece, III

[57] ABSTRACT

This invention relates to the dehydrogenation of a 3-β-hydroxy steroid or a mixture of soy sterols to form the corresponding mixture of Δ4-3-keto derivatives of phytosterols, the improvement which comprises dehydrogenating the said steroid or mixture of sterols using copper or palladium as the catalyst and in the presence of a dialkyl ketone solvent.

16 Claims, No Drawings

PROCESS FOR DEHYDROGENATION OF STEROLS TO PRODUCE Δ4-3-KETOSTEROIDS

This invention relates to the dehydrogenation of a 3-β-hydroxy steroid or a mixture of soy sterols to form the corresponding Δ4-3-keto derivatives of phytosterols using as a catalyst either copper or palladium and using as the solvent a dialkyl ketone.

The naturally occurring phytosterol components of vegetable oils such as soy oils can be used in the preparation of certain pharmaceuticals such as progesterone which itself also can be used to prepare other steroids such as cortisone and the like. However, an economical route to the preparation of progesterone from soy sterols involves first the dehydrogenation of such sterols to the 4-en-3-one derivatives as the initial step. The 3β-OH group of the sterol is dehydrogenated to a ketone group with the rearrangement of the $\Delta^5$ double bond into conjugation with the carbonyl group. Catalytic dehydrogenation is an economical method for such a process. Previously, catalytic dehydrogenation for such conventional transformation was carried out via an Oppenauer oxidation as disclosed by Oppenauer, *Recl. Trav. Chim. Pays-Bas.*, 56, 137 (1937). Another prior art process used Raney nickel for this reaction, either in presence of a high boiling solvent like p-cymene as disclosed by Chakravarti, Chakravarti, and Metra, *Nature*, 193, 1071 (1962) or in the presence of a hydrogen acceptor as disclosed by E. C. Kleiderer, and E. C. Kornfeld, *J. Org. Chem.*, 13, 455 (1948) and Kleiderer, Rice, Conquest and Williams, U.S. Dept. of Commerce, Office of the Publication Board, Report PB 981, 1945. It would therefore be an advance in the state of the art to provide improved processes for the catalytic dehydrogenation of soy sterols.

In accordance with the present invention soy sterols can be dehydrogenated to the corresponding 4-en-3-one derivatives using copper or palladium in the presence of a dialkyl ketone such as methyl ethyl ketone as a solvent.

The dehydrogenation can be carried out over periods of time from about 8 to 30 hours, preferably 10–24 hours, most preferably 14–18. The temperature at which the dehydrogenation is carried out is from 200°–350° C., preferably 250°–325° C., most preferably 275°–300° C. At temperatures lower than 200° C., the rate of hydrogenation is too slow for effective reaction. At temperatures greater than 350° C. dehydration occurs with some decomposition of the soy sterols. The dialkyl ketone solvent can be any lower alkyl ketone such as for example dimethyl ketone, diethyl ketone, dipropyl ketone, dibutyl ketone and the like as well as methyl ethyl ketone, methyl butyl ketone and the like. The amount of solvent used is not critical and depends on whether the process of the present invention is to be operated as a batch process or a continuous process. A greater amount of solvent is generally needed to operate a continuous process, however, an amount of solvent five times the amount of soy sterols employed is generally satisfactory for both types of processes.

The catalyst preferably is a particulate metallic material having a large surface area. Forms of such catalyst therefore can be, for example, in the form of dust or other large surface area forms of copper such as copper wire or gause. The palladium should likewise have a large surface area and should be in the form of sponge or other similar large surface area forms of palladium.

The amount of catalyst employed varies with the amount soy sterol used and the speed of reaction desired for the dehydrogenation reaction. Generally, an amount of catalyst used can be equal to about 20 to 40 percent, preferably 25 to 30 percent, based on the weight of the soy sterols to be dehydrogenated.

This invention can be further illustrated by the following examples, although it will be understood that these examples are included merely for purposes of illustration and are not intended to limit the scope of the invention unless otherwise specifically indicated.

EXAMPLE 1

To 300 g. of mixed soy sterols (~20% stigmasterol) in 1500 ml of methyl ethyl ketone was added 100 g. of copper wire. After heating at 275° C. 16 hrs. in a rocking autoclave, the Δ4-3 keto derivatives of soy sterols were isolated by filtering the catalyst and evaporation of the solvent from the filtrate (isolated 291 g.). The Δ4-3-keto derivatives of soy sterols are then reacted by ozonolysis to form the 4-stigmasten-3-one-derived aldehyde material, 3-ketodinor-4-cholen-22-aldehyde, which can be isolated from the other Δ4-3-keto derivatives of soy sterols by either chromatography or by treatment with sodium bisulfite and extraction with a suitable organic solvent such as toluene.

EXAMPLE 2

To 200 g. of mixed soy sterols (~20% stigmasterol) in 1500 ml of methyl ethyl ketone was added 50 g. of palladium sponge. After heating at 300° C. 8 hrs. in a rocking autoclave, the Δ4-3-keto derivatives of soy sterols were isolated by filtering the catalyst and evaporation of the solvent from the filtrate. Isolated 205 g. of Δ4-3-keto derivatives of soy sterols.

EXAMPLE 3

Cholesterol (24 g), methyl ethyl ketone (150 ml), and copper (6.5 g) were heated and rocked at 275° C. for 8 hrs. An analysis by gas chromatography indicated 60% unreacted cholesterol and 30% 4-cholesten-3-one. The mixture was reheated and rocked at 275° C. for 8 more hours and then the catalyst was filtered and the solvent evaporated in vacuo from the filtrate to give 23 g. solids analyzed by gas chromatography to show 11% cholesterol and 75% 4-cholesten-3-one. Approximately 90% of the cholesterol was converted to 4-cholesten-3-one in 83% yield.

EXAMPLE 4

Cholesterol (20 g), methyl ethyl ketone (150 ml), and palladium sponge (5.0 g) were heated and rocked at 300° C. for 16 hr. Analysis of an aliquot of the reaction solution by gas chromatography showed 9% cholesterol and 91% 4-cholesten-3-one. The catalyst was filtered and the filtrate was concentrated in vacuo to give 20.5 g white solids. Approximately 90% of the cholesterol was converted to 4-cholesten-3-one in the presence of palladium. Similar results can be obtained if cholesterol is replaced with sitosterol.

The process of the present invention provides an improved method for the dehydrogenation of steroids and soy sterols to provide $\Delta^4$-3-ketosteroids. These 4-en-3-ones derivatives can be used to provide materials useful for preparation of valuable steroids such as the cortical steroids.

The invention has been described in detail with particular reference to preferred embodiments thereof, but it will be understood that variations and modifications can be affected within the spirit and scope of the invention.

I claim:

1. A process which comprises dehydrogenating a 3-β-hydroxy steroid or a mixture of soy sterols to form the corresponding Δ4-3-keto derivatives, the improvement which comprises dehydrogenating said steroid or mixture of sterols using either copper or palladum as the catalyst and in the presence of a dialkyl ketone solvent.

2. A process according to claim 1 wherein said 3-β-hydroxy steroid is stigmasterol.

3. A process according to claim 2 wherein said catalyst is copper.

4. A process according to claim 3 wherein said dialkyl ketone is methyl ethyl ketone.

5. A process according to claim 2 wherein said catalyst is palladium.

6. A process according to claim 5 wherein said dialkyl ketone is methyl ethyl ketone.

7. A process according to claim 1 wherein said 3-β-hydroxy steroid is cholesterol.

8. A process according to claim 7 wherein said catalyst is copper.

9. A process according to claim 8 wherein said dialkyl ketone is methyl ethyl ketone.

10. A process according to claim 7 wherein said catayst is palladium.

11. A process according to claim 10 wherein said dialkyl ketone is methyl ethyl ketone.

12. A process according to claim 1 wherein said 3-β-hydroxy steroid is sitosterol.

13. A process according to claim 12 wherein said catalyst is copper.

14. A process according to claim 13 wherein said dialkyl ketone is methyl ethyl ketone.

15. A process according to claim 12 wherein said catalyst is palladium.

16. A process according to claim 15 wherein said dialkyl ketone is methyl ethyl ketone.

* * * * *